(12) United States Patent
Troppmann et al.

(10) Patent No.: US 8,735,321 B2
(45) Date of Patent: May 27, 2014

(54) PROCESS FOR THE PRODUCTION OF PARTICLES COMPRISING ACTIVE AGROCHEMICAL INGREDIENTS IN AMORPHOUS FORM

(75) Inventors: Ulrike Troppmann, Schifferstadt (DE); Winfried Mayer, Bubenheim (DE); Sebastian Koltzenburg, Dannstadt-Schauernheim (DE); Rafel Israels, Cologne (DE); Andreas Bauder, Mannheim (DE); Ulf Schlotterbeck, Mannheim (DE)

(73) Assignee: BASF SE, Ludwigshafen (DE)

( * ) Notice: Subject to any disclaimer, the term of this patent is extended or adjusted under 35 U.S.C. 154(b) by 318 days.

(21) Appl. No.: 12/990,704

(22) PCT Filed: May 6, 2009

(86) PCT No.: PCT/EP2009/055458
§ 371 (c)(1),
(2), (4) Date: Nov. 2, 2010

(87) PCT Pub. No.: WO2009/135865
PCT Pub. Date: Nov. 12, 2009

(65) Prior Publication Data
US 2011/0053772 A1   Mar. 3, 2011

(30) Foreign Application Priority Data
May 9, 2008 (EP) .................................. 08155959

(51) Int. Cl.
| | |
|---|---|
| A01N 43/40 | (2006.01) |
| A61K 31/44 | (2006.01) |
| A01N 43/64 | (2006.01) |
| A01N 43/50 | (2006.01) |
| A01N 43/56 | (2006.01) |
| A01N 25/26 | (2006.01) |
| A01N 37/44 | (2006.01) |
| A61K 31/415 | (2006.01) |
| A61K 31/21 | (2006.01) |
| C07D 211/72 | (2006.01) |
| C07D 213/56 | (2006.01) |
| C07C 69/76 | (2006.01) |
| C07C 229/00 | (2006.01) |

(52) U.S. Cl.
USPC ........... 504/100; 504/118; 504/130; 504/147; 504/139; 514/355; 514/357; 514/383; 514/396; 514/406; 514/407; 514/506; 546/316; 548/371.1; 548/374.1; 548/375.1; 560/45; 560/105

(58) Field of Classification Search
USPC .......... 504/118, 130, 147, 139; 514/355, 357, 514/383, 396, 406, 407, 506; 546/316; 548/371.1, 374.1, 375.1, 383, 396; 560/45, 105
See application file for complete search history.

(56) References Cited

U.S. PATENT DOCUMENTS

| | | | |
|---|---|---|---|
| 4,571,088 A * | 2/1986 | Frensch et al. | 366/136 |
| 2006/0165742 A1* | 7/2006 | Reizlein et al. | 424/405 |
| 2008/0318785 A1* | 12/2008 | Koltzenburg et al. | 504/139 |

FOREIGN PATENT DOCUMENTS

| | | |
|---|---|---|
| EP | 0 145 879 | 6/1985 |
| EP | 0 249 075 | 12/1987 |

(Continued)

OTHER PUBLICATIONS

International Search Report prepared in International Application No. PCT/EP2009/055458, filed May 6, 2009.

(Continued)

*Primary Examiner* — Jane C Oswecki
(74) *Attorney, Agent, or Firm* — Brinks Gilson & Lione

(57) ABSTRACT

An object of the present invention is a process for the preparation of particles which comprise two agrochemical active ingredients in amorphous form, where a melt comprising the two molten agrochemical active ingredients is emulsified in an aqueous solution and cooled. A further object is the use of an agrochemical active ingredient for inhibiting the crystallization of another agrochemical active ingredient in a preparation process for particles which comprise the two agrochemical active ingredients in amorphous form, where a melt comprising the two molten agrochemical active ingredients is emulsified in an aqueous solution and cooled. A further object is particles which comprise two agrochemical active ingredients in amorphous form. The use in plant protection is also described.

18 Claims, 1 Drawing Sheet

(56) References Cited

FOREIGN PATENT DOCUMENTS

| | | | | |
|---|---|---|---|---|
| EP | 1 060 667 | | 4/2004 | |
| JP | 2916703 B2 | * | 7/1999 | |
| JP | 2916703 B2 | * | 7/1999 | ............. A01N 25/00 |
| WO | WO 95 05164 | | 2/1995 | |
| WO | WO95/05164 | * | 2/1995 | ............... A61K 9/14 |
| WO | WO 96 27290 | | 9/1996 | |
| WO | WO03007716 A1 | * | 1/2003 | ........... A01N 43/653 |
| WO | WO 03 034822 | | 5/2003 | |
| WO | WO 2006 111327 | | 10/2006 | |

OTHER PUBLICATIONS

International Preliminary Report on Patentability from corresponding International Application No. PCT/EP2009/055458, filed May 6, 2009.

* cited by examiner

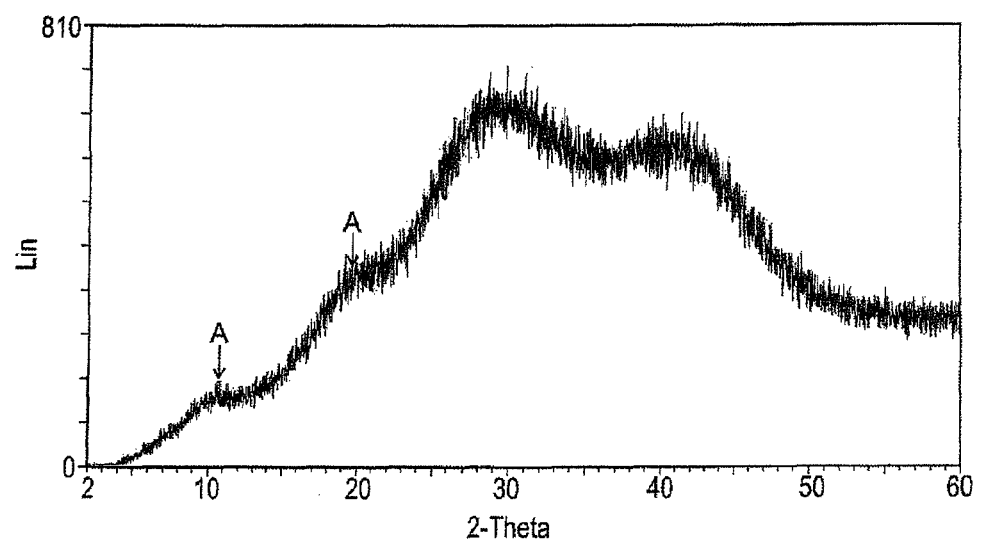

PROCESS FOR THE PRODUCTION OF PARTICLES COMPRISING ACTIVE AGROCHEMICAL INGREDIENTS IN AMORPHOUS FORM

This application is a National Stage application of International Application No. PCT/EP2009/055458 filed May 6, 2009, the entire contents of which is hereby incorporated herein by reference. This application also claims priority under 35 U.S.C. §119 to European Patent Application No. 08155959.3, filed May 9, 2008, the entire contents of which is hereby incorporated herein by reference.

An object of the present invention is a process for the preparation of particles which comprise two agrochemical active ingredients in amorphous form, where a melt comprising the two molten agrochemical active ingredients is emulsified in an aqueous solution and cooled. A further object is the use of an agrochemical active ingredient for inhibiting the crystallization of another agrochemical active ingredient in a preparation process for particles which comprise the two agrochemical active ingredients in amorphous form, where a melt comprising the two molten agrochemical active ingredients is emulsified in an aqueous solution and cooled. A further object is particles which comprise two agrochemical active ingredients in amorphous form. Moreover, an object is a method of controlling phytopathogenic fungi and/or undesirable vegetation and/or undesirable attack by insects or mites and/or for the regulation of the growth of plants. Another object is a method of controlling undesirable attack by insects or mites on plants, and/or of controlling phytopathogenic fungi and/or of controlling undesirable vegetation. Finally, one object relates to seed which has been dressed with the agrochemical formulation. Combinations of preferred features with other preferred features are comprised by the present invention.

In the preparation of formulations of plant protectants to give suspensions or suspoemulsions, it is usual to incorporate, in a vessel, one or more active components into aqueous solutions with the aid of a stirring apparatus. Thereafter, the crude batch is comminuted finely. Depending on the desired fineness and millability of the starting materials, a further comminution with specific mills follows. Depending on the millability of the active ingredients, different milling times are required for the comminution.

If it is intended to formulate an active ingredient mixture, the milling time required depends, in the case of such a co-milling process, on the component with the poorest millability. In bad cases, over-milling of sensitive active ingredients, i.e. product damage, may occur during the time required for milling the hardest component. When starting materials with different millability are comminuted, it may therefore be advantageous to mill, or to emulsify, the starting materials separately of one another and only then to prepare a mixture of the active ingredient suspensions or active ingredient emulsions. It is characteristic of such mixtures that the active ingredient components are largely separate from one another in the suspension particles or emulsion drops.

For example, epoxiconazole is present in various formulations in the form of mixtures with other agrochemical active ingredients. Due to the high melting point of epoxiconazole (135° C.), the melt cannot readily be comminuted in aqueous systems in the form of a melt emulsification.

WO 2006/111327 discloses for example a preparation comprising a mixture of conazole with a further plant protectant and a copolymer which comprises a monoethylenically unsaturated monomer having a sulfonic acid group. This copolymer is necessary because it brings about the stabilization of the active ingredient in the aqueous phase and is present in the melt of the active ingredient.

Synthesis and solidification generate many active ingredients in a crystalline modification with unsatisfactory or poor biological activity. The above-described comminution mechanisms only reduce the size of the crystals, thereby barely improving the bioavailability. Moreover, the result of the comminution, when accompanied with insufficient stabilization of the system, may be adversely affected, or reversed, by maturation effects of the crystalline particles.

Processes for the preparation of particles which comprise two agrochemical active ingredients in amorphous form, where a melt comprising the two molten agrochemical active ingredients is emulsified in an aqueous solution and cooled, are known.

EP 1 060 667 B1 discloses a preparation process for suspension concentrates of crystalline pesticide mixtures in which a pesticide melt is combined with a solvent stream. Crystallization enhancers or inhibitors may be added.

EP 0 249 075 B1 discloses a preparation process for aqueous suspension concentrates of pendimethalin. Here, the aqueous dispersion of molten pendimethalin is treated with 0 to 50% by volume of at least one secondary pesticide and the mixture is ground.

EP 0 145 879 B1 discloses a preparation process for aqueous plant protectant dispersions which may comprise one or more active ingredients. Here, a molten active ingredient is metered into the exit jet of a nozzle, which jet comprises an aqueous solution.

WO 95/05164 discloses a melt emulsification of sparingly soluble active ingredients and their mixtures for the preparation of amorphous particles. Crystallization inhibitors may be employed in this method.

Furthermore, WO 1996/27290 discloses the use of a fungicidal triazole in an effective amount in order to inhibit the crystallization of 5-methyl-5-(4-phenoxyphenyl)-3-(phenylamino)-2,4-oxazolidinedione.

BRIEF DESCRIPTION OF THE DRAWING

FIG. 1 shows an X-ray diffraction pattern of particles comprising pyraclostrobin, epoxiconazole and emulsifier 1 in a sample holder and covered with Styroflex film using a diffractometer D 5000 (at 25°C.; step size 0.020 degrees; step time 4.8 s; Cu anode).

It was an object of the present invention to provide a novel process for the preparation of particles which comprise two agrochemical active ingredients in amorphous form. It was intended that the novel process make possible the preparation of an agrochemical formulation with a higher and/or more rapid biological activity than known formulations. Furthermore, it was an object that the formulation be largely free from conventional, especially polymeric, crystallization inhibitors to make the formulation as environmentally compatible as possible. A further aspect of the object was to formulate solid agrochemical active ingredients which are sparingly soluble in water in such a way that they have a higher and/or more rapid biological activity than shown by traditional formulations. Furthermore, it was an object to formulate mixtures of pyraclostrobin and epoxiconazole with high and/or rapid biological activity. It was a further object to provide stable aqueous formulations comprising prochloraz.

The object was achieved by a process for the preparation of particles which comprise two agrochemical active ingredients in amorphous form, where a melt comprising the two molten agrochemical active ingredients is emulsified in an aqueous solution and cooled, during which process the one agrochemical active ingredient inhibits the crystallization of the other agrochemical active ingredient.

In general, the particles comprise two agrochemical active ingredients. Usually, these take the form of two different active ingredients. However, the particles may also comprise three or even more active ingredients. It is preferred that the particles comprise precisely two active ingredients. In a further embodiment, the particles may be unencapsulated. This means that they are free from a polymeric coating.

Particles are generally understood as meaning particles which are solid at 20° C. Depending on the use, the particles may differ in size or size distribution. In general, the particles have a particle size distribution with an $x_{50}$ value of from 0.05 µm to 10 µm, preferably from 0.2 µm to 5 µm and especially preferably from 0.5 µm to 2 µm. The particle size distribution can be determined by laser light diffraction of an aqueous suspension comprising the particles. The sample preparation, for example the dilution to the measuring concentration, depends in this measuring method on the fineness and concentration of the active ingredients in the suspension sample and on the instrumentation used, inter alia. The procedure must be adapted to suit the system in question and is known to the skilled worker.

Amorphous means that the molecular units of a homogeneous solid are not arranged in the form of crystal lattices. An amorphous form of an active ingredient means that it is largely free from crystalline material, it being preferred that 80 to 100% by weight, in particular 90 to 100% by weight, of the material is in amorphous form. Amorphous forms can be distinguished from crystalline forms by a variety of methods, for example by viewing under the microscope in polarized light, differential scanning calorimetry, X-ray diffraction or solubility comparisons. The choice of method depends, for example, on the fineness of the particles. Thus, viewing under the light microscope in polarized light can only be done when a substantial fraction of the particles is big enough to be able to be resolved by the microscope, that is to say in a range of above approximately 1 µm. The determination to what extent an amorphous form is present is carried out after the preparation process according to the invention has ended, in particular after the fine emulsion has been prepared and cooled. It is possible that the form of the particles changes after the preparation, so that the determination is preferably carried out within one hour, especially preferably 24 h, in particular 72 h.

The amorphous form of epoxiconazole or pyraclostrobin can be distinguished for example from the crystalline form by viewing an aqueous suspension under the microscope in polarized light. To this end, the original suspension must, depending on the starting concentration and the fineness of the active ingredient, be diluted with fully demineralized water so that the particles can be prepared on the slide in such a way that they are presented as isolated from one another as possible. For example, a ten percent strength active ingredient formulation with a mean particle size of from approximately 1 to 2 µm must be diluted approximately by a factor of 60 to 80. The dilution step, and also the analysis, are normally carried out at room temperature. Here, the amorphous particles appear as spherical particles, while crystalline particles appear for example as crystals with corners or right angles, or else as needles.

In accordance with the invention, the one agrochemical active ingredient inhibits the crystallization of the other agrochemical active ingredient. The property of an active ingredient to inhibit the crystallization of one or more other active ingredients can be identified in simple preliminary tests. To this end, the active ingredients are mixed with one another in different amounts, preferably in the range of from 1 to 100 g, and converted into a homogeneous melt by warming to above the melting point of the mixture. Thereafter, the melt is allowed to cool, preferably by allowing the melt to stand at room temperature. After the melt has cooled, preferably one hour after cooling to room temperature, it is possible to identify, with the aid of a light microscope or differential scanning calorimetry (DSC), whether the solidified melt comprises crystals. The DSC analysis is preferred. To this end, a sample is generally heated once in an aluminum pan at a heating rate of from 5 to 20, preferably 10 K/min. The starting temperature is usually 50° C. under the expected melting point, and the end temperature 20° C. above. Further principles of the DSC measurement follow DIN 51004 (June 1994) "Bestimmung der Schmelztemperaturen kristalliner Stoffe mit der Differenzthermoanalyse" [Determination of melting temperatures of crystalline materials using differential thermal analysis].

When a melting range of at least 10° C., preferably at least 20° C. and in particular at least 30° C. is found, then the crystallization-inhibitory property is identified. Alternatively, the crystallization-inhibitory property can be identified when the mixture of the active ingredients no longer shows first-order phase transitions upon heating. In a typical DSC plot, these phase transitions are revealed as peaks. In the ideal case, amorphous phases show no peaks in DSC, but only a second-order phase transition in the form of a step, which is referred to as glass transition temperature. In contrast to this ideal behavior, even the DSC plots of amorphous phases can reveal peaks, in particular around the glass transition temperature, as the result of local superstructure formation. To decide whether a mixture phase is amorphous, it is therefore essential that peaks are no longer present in the range of the melting points of the pure active ingredients, or else at most substantially smaller peaks with an area which corresponds to no more than 10% of the area of the crystallization peak of the pure active ingredient.

As an alternative to heating above the melting point of the mixture, the active ingredients may be dissolved separately in a suitable solvent, the active-ingredient-comprising solutions may be mixed and the solvents may subsequently be removed. The further analysis of crystals is performed as described hereinabove. It is possible to employ one or more different solvents in order to dissolve the respective active ingredient. It is preferred to employ solvents in which the respective active ingredient is soluble to at least 10% by weight at 20° C. In most cases, the solvents have a boiling point of below 100° C., preferably below 70° C., at 1013 mbar. The solvents may be removed at temperatures of up to 100° C., preferably up to 60° C., and especially preferably up to 30° C.

The preferred method is heating above the melting point of the mixture.

In a further preferred embodiment, the crystallization-inhibiting activity of the one agrochemical active ingredient on the other agrochemical active ingredient is determined by a) mixing the active ingredients with each other, converting them into a homogeneous melt by heating above the melting point of the mixture, and allowing the melt to cool; or b) dissolving the active ingredients separately in a solvent, mixing the active-ingredient-comprising solutions and subsequently removing the solvent;

and, subsequently determining with the aid of a light microscope or dynamic differential scanning calorimetry (DSC) whether the solidified melt or the dried mixture comprises crystals.

In this context, the term agrochemical active ingredient, or pesticide, refers to at least one active ingredient selected from the group of the insecticides, fungicides, herbicides, safeners and/or growth regulators.

The following list of fungicides identifies possible active ingredients, but is not intended to be limited thereto:

A) strobilurins:
- azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methylphenoxy)-5-fluoropyrimidin-4-yloxy)phenyl)-2-methoxyimino-N-methyl-acetamide, methyl 2-(ortho-((2,5-dimethylphenyl-oxymethylene)phenyl)-3-methoxyacrylate, 3-methoxy-2-(2-(N-(4-methoxyphenyl)-cyclopropanecarboximidoylsulfanylmethyl)phenyl) acrylic acid methyl ester, 2-(2-(3-(2,6-dichlorophenyl)-1-methyl-allylideneaminooxymethyl)phenyl)-2-methoxyimino-N-methyl-acetamide;

B) carboxamides:
- carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M, ofurace, oxadixyl, oxycarboxin, penthiopyrad, tecloftalam, thifluzamide, tiadinil, 2-amino-4-methylthiazole-5-carboxanilide, 2-chloro-N-(1,1,3-trimethyl-indan-4-yl)nicotinamide, N-(2',4'-difluorobiphenyl-2-yl)-3-difluoromethyl-1-methyl-1H-pyrazole-4-carboxamide, N-(2',4'-dichlorobiphenyl-2-yl)-3-difluoromethyl-1-methyl-1H-pyrazole-4-carboxamide, N-(2',5'-difluorobiphenyl-2-yl)-3-difluoromethyl-1-methyl-1H-pyrazole-4-carboxamide, N-(2',5'-dichlorobiphenyl-2-yl)-3-difluoromethyl-1-methyl-1H-pyrazole-4-carboxamide, N-(3',5'-difluorobiphenyl-2-yl)-3-difluoromethyl-1-methyl-1H-pyrazole-4-carboxamide, N-(3',5'-dichlorobiphenyl-2-yl)-3-difluoromethyl-1-methyl-1H-pyrazole-4-carboxamide, N-(3'-fluorobiphenyl-2-yl)-3-difluoromethyl-1-methyl-1H-pyrazole-4-carboxamide, N-(3'-chlorobiphenyl-2-yl)-3-difluoromethyl-1-methyl-1H-pyrazole-4-carboxamide, N-(2'-fluorobiphenyl-2-yl)-3-difluoromethyl-1-methyl-1H-pyrazole-4-carboxamide, N-(2'-chlorobiphenyl-2-yl)-3-difluoromethyl-1-methyl-1H-pyrazole-4-carboxamide, N-(3',4',5'-trifluorobiphenyl-2-yl)-3-difluoromethyl-1-methyl-1H-pyrazole-4-carboxamide, N-(2',4',5'-trifluorobiphenyl-2-yl)-3-difluoromethyl-1-methyl-1H-pyrazole-4-carboxamide, N-[2-(1,1,2,3,3,3-hexafluoropropoxy)-phenyl]-3-difluoromethyl-1-methyl-1H-pyrazole-4-carboxamide, N-[2-(1,1,2,2-tetrafluoroethoxy)-phenyl]-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(3',4'-dichloro-5-fluorobiphenyl-2-yl)-3-difluoromethyl-1-methyl-1H-pyrazole-4-carboxamide, N-(2-(1,3-dimethylbutyl)-phenyl)-1,3,3-trimethyl-5-fluoro-1H-pyrazole-4-carboxamide, N-(4'-chloro-3',5'-difluorobiphenyl-2-yl)-3-difluoromethyl-1-methyl-1H-pyrazole-4-carboxamide, N-(4'-chloro-3',5'-difluorobiphenyl-2-yl)-3-trifluoromethyl-1-methyl-1H-pyrazole-4-carboxamide, N-(3',4'-dichloro-5'-fluorobiphenyl-2-yl)-3-trifluoromethyl-1-methyl-1H-pyrazole-4-carboxamide, N-(3',5'-difluoro-4'-methylbiphenyl-2-yl)-3-difluoromethyl-1-methyl-1H-pyrazole-4-carboxamide, N-(3',5'-difluoro-4'-methylbiphenyl-2-yl)-3-trifluoromethyl-1-methyl-1H-pyrazole-4-carboxamide, N-(2-bicyclopropyl-2-yl-phenyl)-3-difluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoromethyl-1-methyl-1H-pyrazole-4-carboxamide;
- carboxylic acid morpholides: dimethomorph, flumorph;
- benzamides: flumetover, fluopicolide, fluopyram, zoxamid, N-(3-ethyl-3,5,5-trimethylcyclohexyl)-3-formylamino-2-hydroxybenzamide;
- other carboxamides: carpropamid, diclocymet, mandipropamid, oxytetracyclin, silthiofam, N-(6-methoxypyridin-3-yl)cyclopropanecarboxamide;

C) azoles:
- triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chlorophenyl)-2-([1,2,4]triazol-1-yl)-cycloheptanol;
- imidazoles: cyazofamid, imazalil, imazalil sulfate, pefurazoate, prochloraz, triflumizole;
- benzimidazoles: benomyl, carbendazim, fuberidazole, thiabendazole;
- others: ethaboxam, etridiazole, hymexazole, 2-(4-chlorophenyl)-N-[44-(3,4-dimethoxyphenyl)isoxazol-5-yl]-2-prop-2-ynyloxyacetamide;

D) nitrogen-comprising heterocyclyl compounds
- pyridines: fluazinam, pyrifenox, 3-[5-(4-chlorophenyl)-2,3-dimethylisoxazolidin-3-yl]-pyridine, 3-[5-(4-methylphenyl)-2,3-dimethylisoxazolidin-3-yl]-pyridine, 2,3,5,6-tetrachloro-4-methanesulfonylpyridine, 3,4,5-trichloropyridine-2,6-dicarbonitrile, N-(1-(5-bromo-3-chloropyridin-2-yl)ethyl)-2,4-dichloronicotinamide, N-((5-bromo-3-chloropyridin-2-yl)methyl)-2,4-dichloronicotinamide;
- pyrimidines: bupirimate, cyprodinil, diflumetorim, fenarimol, ferimzone, mepanipyrim, nitrapyrin, nuarimol, pyrimethanil;
- piperazines: triforine;
- pyrroles: fludioxonil, fenpiclonil;
- morpholines: aldimorph, dodemorph, dodemorph acetate, fenpropimorph, tridemorph;
- piperidines: fenpropidin;
- dicarboximides: fluorimide, iprodione, procymidone, vinclozolin;
- nonaromatic 5-membered heterocycles: famoxadone, fenamidone, octhilinone, probenazole, S-allyl 5-amino-2-isopropyl-3-oxo-4-orthotolyl-2,3-dihydropyrazole-1-thio carboxylate;
- others: acibenzolar-S-methyl, amisulbrom, anilazine, blasticidin-S, captafol, captan, quinomethionate, dazomet, debacarb, diclomezine, difenzoquat, difenzoquat methylsulfate, fenoxanil, folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)-[1,2,4]triazolo[1,5-a]pyrimidine, 6-(3,4-dichlorophenyl)-5-methyl-[1,2,4]triazolo[1,5-a]pyrimidin-7-ylamine, 6-(4-tert-butylphenyl)-5-methyl[1,2,4]triazolo[1,5-a]pyrimidin-7-ylamine, 5-methyl-6-(3,5,5-trimethylhexyl)-[1,2,4]triazolo[1,5-a]pyrimidin-7-ylamine, 5-methyl-6-octyl-

[1,2,4]triazolo[1,5-a]pyrimidin-7-ylamine, 6-methyl-5-octyl-[1,2,4]triazolo[1,5-a]pyrimidin-7-ylamine, 6-ethyl-5-octyl-[1,2,4]triazolo[1,5-a]pyrimidin-7-ylamine, 5-ethyl-6-octyl-[1,2,4]triazolo[1,5-a]pyrimidin-7-ylamine, 5-ethyl-6-(3,5,5-trimethylhexyl)-[1,2,4]triazolo[1,5-a]pyrimidin-7-ylamine, 6-octyl-5-propyl-[1,2,4]triazolo[1,5-a]pyrimidin-7-ylamine, 5-methoxymethyl-6-octyl-[1,2,4]triazolo[1,5-a]pyrimidin-7-ylamine, 6-octyl-5-trifluoromethyl-[1,2,4]triazolo[1,5-a]pyrimidin-7-ylamine and 5-trifluoromethyl-6-(3,5,5-trimethylhexyl)-[1,2,4]triazolo[1,5-a]pyrimidin-7-ylamine;

E) carbamates and dithiocarbamates thio- and dithiocarbamates: ferbam, mancozeb, maneb, metam, methasulphocarb, metiram, propineb, thiram, zineb, ziram;

carbamates: diethofencarb, benthiavalicarb, iprovalicarb, propamocarb, propamocarb hydrochloride, valiphenal, 4-fluorophenyl N-(1-(1-(4-cyanophenyl)ethanesulfonyl)-but-2-yl)carbamate;

F) other fungicides guanidines: dodine, dodine free base, guazatine, guazatine acetate, iminoctadine, iminoctadine triacetate, iminoctadine tris(albesilate);

antibiotics: kasugamycin, kasugamycin hydrochloride hydrate, polyoxins, streptomycin, validamycin A;

nitrophenyl derivatives: binapacryl, dicloran, dinobuton, dinocap, nitrothal-isopropyl, tecnazene;

organometal compounds: fentin salts such as, for example, fentin acetate, fentin chloride, fentin hydroxide;

sulfur-comprising heterocyclyl compounds: dithianon, isoprothiolane;

organophosphorus compounds: edifenphos, fosetyl, fosetyl-aluminum, iprobenfos, phosphorous acid and its salts; pyrazophos, tolclofos-methyl;

organochlorine compounds: chlorthalonil, dichlofluanid, dichlorophen, flusulfamide, hexachlorobenzene, pencycuron, pentachlorophenol and its salts, phthalide, quintozene, thiophanate-methyl, tolylfluanid, N-(4-chloro-2-nitrophenyl)-N-ethyl-4-methylbenzenesulfonamide;

inorganic active ingredients: phosphorous acid and its salts, Bordeaux mixture, copper salts such as, for example, copper acetate, copper hydroxide, copper oxychloride, basic copper sulfate, sulfur;

others: biphenyl, bronopol, cyflufenamid, cymoxanil, diphenylamine, metrafenone, mildiomycin, oxine-copper, prohexadione-calcium, spiroxamine, tolylfluanid, N-(cyclopropylmethoxyimino-(6-difluoromethoxy-2,3-difluorophenyl)methyl)-2-phenylacetamide, N'-(4-(4-chloro-3-trifluoromethylphenoxy)-2,5-dimethylphenyl)-N-ethyl-N-methylformamidine, N'-(4-(4-fluoro-3-trifluoromethylphenoxy)-2,5-dimethylphenyl)-N-ethyl-N-methylformamidine, N'-(2-methyl-5-trifluoromethyl-4-(3-trimethylsilanylpropoxy)phenyl)-N-ethyl-N-methylformamidine, N'-(5-difluoromethyl-2-methyl-4-(3-trimethylsilanylpropoxy)phenyl)-N-ethyl-N-methylformamidine;

G) growth regulators abscisic acid, amidochior, ancymidol, 6-benzylaminopurine, brassinolide, butralin, chlormequat (chlormequat chloride), cholin chloride, cyclanilide, daminozide, dikegulac, dimethipin, 2,6-dimethylpuridine, ethephone, flumetralin, flurprimidol, fluthiacet, forchlorfenuron, gibberellic acid, inabenfid, indole-3-acetic acid, maleic hydrazide, mefluidide, mepiquat (mepiquat chloride), metconazole, naphthalene acetic acid, N-6-benzyladenine, paclobutrazole, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole.

The following list of herbicides identifies possible active ingredients, but is not intended to be restricted to these:

acetamides: acetochlor, alachlor, butachlor, dimethachior, dimethenamid, flufenacet, mefenacet, metolachlor, metazachlor, napropamide, naproanilide, pethoxamid, pretilachior, propachlor, thenylchlor;

amino acid analogs: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

bipyridyls: diquat, paraquat;

carbamates and thiocarbamates: asulam, butylate, carbetamide, desmedipham, dimepiperate, eptam (EPTC), esprocarb, molinate, orbencarb, phenmedipham, prosulfocarb, pyributicarb, thiobencarb, tri-allate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bromoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxy acetic acid (2,4-D), 2,4-DB, dichlorprop, MCPA, MCPA-thioethyl, MCPB, mecoprop;

pyrazines: chioridazon, flufenpyr-ethyl, fluthiacet, norflurazone, pyridate;

pyridines: aminopyralid, clopyralid, diflufenican, dithiopyr, fluridone, fluroxypyr, picloram, picolinafen, thiazopyr, thiazopyr;

sulfonylureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propylimidazo[1,2-b]pyridazin-3-yl)sulfonyl)-3-(4,6-dimethoxypyrimidin-2-yl)urea;

triazines: ametryn, atrazine, cyanazine, dimethametryn, ethiozine, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethlyl, chlorthal, cinmethylin, clomazone, cumyluron, cyprosulfamide, dicamba, difenzoquat, diflufenzopyr, *Drechslera monoceras,* endothal, ethofumesate, etobenzanid, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methylarsonic acid, naptalam, oxadiargyl, oxadiazon, oxaziclomefone, pentoxazone, pinoxaden, pyraclonil, pyraflufen-ethyl, pyrasulfotol, pyrazoxyfen, pyrazolynate, quinoclamine, saflufenacil, sulcotrion, sulfentrazone, terbacil, tefuryltrione, tembotrione, thiencarbazone, topramezone, 4-hydroxy-3-[2-(2-methoxyethoxymethyl)-6-trifluoromethylpyridine-3-carbonyl]bicyclo[3.2.1]oct-3-en-2-one, ethyl (3-[2-chloro-4-fluoro-5-(3-methyl-2,6-dioxo-4-trifluoromethyl-3,6-dihydro-2H-pyrimidin-1-yl) phenoxy]pyridin-2-yloxy)acetate, methyl 6-amino-5-chloro-2-cyclopropylpyrimidine-4-carboxylate, 6-chloro-3-(2-cyclopropyl-6-methylphenoxy)-pyridazin-4-ol, 4-amino-3-chloro-6-(4-chlorophenyl)-5-fluoropyridine-2-carboxylic acid, methyl 4-amino-3-chloro-6-(4-chloro-2-fluoro-3-methoxyphenyl) pyridine-2-carboxylate, and methyl 4-amino-3-chloro-6-(4-chloro-3-dimethylamino-2-fluoro-phenyl) pyridine-2-carboxylate.

The following list of insecticides identifies possible active ingredients, but is not intended to be limited thereto:

organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aidicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin, insect growth inhibitors: a) chitin synthesis inhibitors: benzoylureas: chlorofluazuron, cyramazine, diflubenzuron, flucycloxuron, flufenoxuron, hexaflumuron, lufenuron, novaluron, teflubenzuron, triflumuron; buprofezin, diofenolan, hexythiazox, etoxazole, clofentazin; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramate;

nicotine receptor agonists/antagonists: clothianidin, dinotefuran, imidacloprid, thiamethoxam, nitenpyram, acetamiprid, thiacloprid, 1-(2-chlorothiazol-5-ylmethyl)-2-nitrimino-3,5-dimethyl[1,3,5]triazinane;

GABA antagonists: endosulfan, ethiprole, fipronil, vaniliprole, pyrafluprole, pyriprole, 5-amino-1-(2,6-dichloro-4-methylphenyl)-4-sulfinamoyl-1H-pyrazole-3-thiocarboxamide;

macrocyclic lactones: abamectin, emamectin, milbemectin, lepimectin, spinosad, spinetoram;

mitochondrial electron transport chain inhibitor (METI) I acaricides: fenazaquin, pyridaben, tebufenpyrad, tolfenpyrad, flufenerim;

METI II and III substances: acequinocyl, fluacyprim, hydramethylnon;

decouplers: chlorfenapyr;

oxidative phosphorylation inhibitors: cyhexatin, diafenthiuron, fenbutatin oxide, propargite;

insect molting inhibitors: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86); cyenopyrafen, flupyrazofos, cyflumetofen, amidoflumet, imicyafos, bistrifluron and pyrifluquinazon.

The following list shows possible safeners, but is not intended to be limited thereto: benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloroacetyl)-1,3-oxazolidine (R-29148), 4-(dichloroacetyl)-1-oxa-4-azaspiro[4.5]decane (AD-67; MON 4660) and oxabetrinil.

The following list of compounds with growth-regulatory activity shows possible active ingredients, but is not intended to be limited thereto: 1-naphthylacetamide, 1-naphthylacetic acid, 2-naphthyloxyacetic acid, 3-CPA, 4-CPA, ancymidol, anthraquinone, BAP, butifos; tribufos, butralin, chlorflurenol, chlormequat, clofencet, cyclanilide, daminozide, dicamba, dikegulac-sodium, dimethipin, chlorfenethol, etacelasil, ethephone, ethychlozate, fenoprop, 2,4,5-TP, fluoridamid, flurprimidol, flutriafol, gibberellic acid, gibberellin, guazatine, imazalil, indolylbutyric acid, indolylacetic acid, karetazan, kinetin, lactidichior-ethyl, maleic hydrazide, mefluidide, mepiquat chloride, naptalam, paclobutrazole, prohexadione-calcium, quinmerac, sintofen, tetcyclacis, thidiazuron, triiodobenzoic acid, triapenthenol, triazethan, tribufos, trinexapac-ethyl, uniconazole.

The agrochemical active ingredients are preferably selected from the list of the abovementioned agrochemical active ingredients. In a further embodiment, the agrochemical active ingredient is no 5-methyl-5-(4-phenoxyphenyl)-3-(phenylamino)-2,4-oxazolidinedione. In a further embodiment, the agrochemical active ingredient is no fungicidal triazole. Particularly preferably, at least one of the agrochemical active ingredients is metconazole, pyraclostrobin, epoxiconazole or prochloraz. In particular, the agrochemical active ingredients are pyraclostrobin and epoxiconazole, or pyraclostrobin and prochloraz.

In a further preferred embodiment, at least one of the agrochemical active ingredients is metconazole, pyraclostrobin, epoxiconazole, prochloraz, triticonazole, boscalid, N-(3',4',5'-trifluorobiphenyl-2-yl)-3-difluoromethyl-1-methyl-1H-pyrazole-4-carboxamide or metalaxyl.

In a further preferred embodiment, the agrochemical active ingredients comprise pyraclostrobin and epoxiconazole, pyraclostrobin and prochloraz, prochloraz and triticonazole, pyraclostrobin and metconazole, pyraclostrobin and boscalid, pyraclostrobin and metalaxyl, triticonazole and epoxiconazole, triticonazole and metalaxyl, epoxiconazole and metconazole, epoxiconazole and boscalid, N-(3',4',5'-trifluorobiphenyl-2-yl)-3-difluoromethyl-1-methyl-1H-pyrazole-4-carboxamide and triticonazole, N-(3',4',5'-trifluorobiphenyl-2-yl)-3-difluoromethyl-1-methyl-1H-pyrazole-4-carboxamide and metconazole, or pyraclostrobin, metalaxyl and triticonazole. The agrochemical active ingredients especially preferably comprise pyraclostrobin and epoxiconazole, pyraclostrobin and prochloraz, prochloraz and triticonazole or pyraclostrobin and metalaxyl. The abovementioned mixtures consist in particular of the two agrochemical active ingredient mentioned in each case.

The weight ratio in which the agrochemical active ingredients can be employed depends usually on the crystallization-inhibitory activity of the agrochemical active ingredient employed as crystallization inhibitor. When, for example, the abovementioned preliminary experiments have shown that crystallization is inhibited at a certain weight ratio, this weight ratio is suitable. Preferably, the crystallization-inhibitory active ingredient is present in a concentration of at least 5% by weight, specifically at least 10% by weight, based on the total amount of active ingredient. Preferably, each of the active ingredients is present in a concentration of at least 5% by weight, specifically at least 10% by weight, based on the total amount of active ingredient. Especially preferably, the agrochemical active ingredients pyraclostrobin and epoxiconazole are present in a weight ratio of from 5:95 to 95:5, in particular 10:90 to 90:10 and specifically 50:50 to 90:10, or pyraclostrobin and prochloraz in a weight ratio of from 5:95 to 95:5, in particular 10:90 to 90:10 and specifically 10:90 to 50:50. In further embodiments, the following active ingredients are present in the following weight ratios:
- prochloraz and triticonazole: 95:5 to 50:50, in particular 90:10 to 70:30 and specifically 85:15 to 75:25;
- pyraclostrobin and metconazole: 95:5 to 20:80, in particular 90:10 to 30:70 and specifically 85:15 to 35:65;
- pyraclostrobin and boscalid: 95:5 to 50:50, in particular 90:10 to 70:30 and specifically 85:15 to 75:25;
- pyraclostrobin and metalaxyl: 95:5 to 20:80, in particular 90:10 to 30:70 and specifically 85:15 to 35:65;
- triticonazole and epoxiconazole: 80:20 to 20:80, in particular 70:30 to 30:70 and specifically 65:35 to 35:65;
- triticonazole and metalaxyl: 40:80 to 5:95, in particular 30:70 to 10:90 and specifically 25:75 to 15:85;
- epoxiconazole and metconazole: 60:40 to 5:95, in particular 50:50 to 10:90 and specifically 45:55 to 15:85;
- epoxiconazole and boscalid: 60:40 to 20:80, in particular 50:50 to 30:70 and specifically 45:55 to 35:65;
- N-(3',4',5'-trifluorobiphenyl-2-yl)-3-difluoromethyl-1-methyl-1H-pyrazole-4-carboxamide and triticonazole: 60:40 to 20:80, in particular 50:50 to 30:70 and specifically 45:55 to 35:65;
- N-(3',4',5'-trifluorobiphenyl-2-yl)-3-difluoromethyl-1-methyl-1H-pyrazole-4-carboxamide and metconazole: 30:70 to 5:95, in particular 40:60 to 10:90 and specifically 45:55 to 15:85;
- pyraclostrobin, metalaxyl and triticonazole: in one embodiment 20:75:5 to 20:40:40, in particular 20:70:10 to 20:50:30; in a further embodiment 40:40:20 to 5:75:20, in particular 30:50:20 to 10:70:20, in a further embodiment 35:60:5 to 5:60:35, in particular 30:60:10 to 10:60:30.

In a preferred embodiment, agrochemical active ingredients which are sparingly soluble in water are employed. It is preferred to employ active ingredients which are soluble in water at 20° C. to not more than 5% by weight, preferably not more than 1% by weight, especially preferably not more than 0.1% by weight and very specifically not more than 0.01%. In a further preferred embodiment, at least one of the active ingredients is soluble in water at 20° C. to not more than 5% by weight, preferably to not more than 1% by weight, and at least one other active ingredient to not more than 0.1% by weight, preferably not more than 0.01% by weight.

The agrochemical active ingredients which are employed are usually solids at 20° C. The melting point of the active ingredients is preferably at least 30° C. and preferably at least 40° C. In a further embodiment, at least one of the active ingredients has a melting point of not more than 170° C., preferably not more than 150° C., especially preferably not more than 110° C. Usually, at least one of the active ingredients has a melting point of from 20 to 110° C., preferably 30 to 90° C. and specifically 40 to 70° C.

The present invention relates to a process for the preparation of particles which comprise two agrochemical active ingredients in amorphous form, where a melt comprising the two molten agrochemical active ingredients is emulsified in an aqueous solution and cooled, during which process the one agrochemical active ingredient inhibits the crystallization of the other agrochemical active ingredient.

In a preferred embodiment, the melt can be emulsified in an aqueous solution by melting at least two agrochemical active ingredients and introducing this melt into the aqueous solution. To this end, one active ingredient with a low, preferably the lowest, melting point or melting range may be heated and molten. A second and, if appropriate, a further active ingredient may be dissolved or molten in this melt, so that a melt comprising an active ingredient mixture is generated. The melt of the first active ingredient usually acts as the solvent for the further active ingredient(s). Thereafter, the melt is introduced into the aqueous solution, preferably while providing energy. For example, energy can be provided by shaking, stirring, turbulent mixing, injecting a fluid into another, oscillations and cavitation of the mixture (for example using ultrasound), emulsifying centrifuges, colloid mills, sprocket dispersers or homogenizers. In general, the temperature differential between melt and aqueous phase is from 0 to 200° C. Preferably, the melt is 20 to 200° C. warmer than the aqueous phase. Under certain circumstances, these processes must be carried out in pressurized apparatuses since the vapor pressure of the continuous phase rises as the result of the increase in temperature, and may also be above the ambient pressure.

In a further preferred embodiment, the melt can be emulsified in an aqueous solution by melting at least two active ingredients direct in an aqueous solution while providing energy. In the above embodiment, both the continuous phase comprising the aqueous solution and the disperse phase comprising the molten agrochemical active ingredients may be treated with the relevant adjuvants required for the formulation and the later use, such as surfactants.

Once the continuous phase comprising the aqueous solution and the disperse phase comprising the molten agrochemical active ingredients have been combined with one another and preemulsified to give a coarse dispersion, the product is said to be a crude emulsion. The crude emulsion can then be treated in an emulsifier, where the droplets of the disperse phase are divided finely (so-called fine emulsification). The fine-emulsification process step can be carried out batchwise, for example in a stirred vessel, or continuously. Continuously operating machines and apparatuses for making emulsions are known to the skilled worker. Examples are colloid mills, sprocket dispersers and other embodiments of dynamic mixers, furthermore high-pressure homogenizers, pumps with downstream nozzles, valves, membranes or other narrow slit geometries, static mixers, in-line mixers using the rotor-stator principle (Ultra-Turrax, inline dissolver), micromixing systems and ultrasonic emulsifiers. It is preferred to employ sprocket dispersers or high-pressure homogenizers.

After the fine emulsification, the fine emulsion can be cooled to below the melting point or melting range of the active ingredient. This step can be carried out by cooling with stirring (batch operation) or by passing the fine emulsion through a heat exchanger (continuous operation). During this process, the agrochemical active ingredients in the disperse phase solidify in particulate amorphous form.

In a preferred embodiment, the melt which has been introduced into an aqueous solution is cooled at a cooling rate of at least 0.5 K/min with the aid of a controllable cooling apparatus. A controllable cooling apparatus comprises, for example, a tube which is capable of being cooled and through which the substances to be cooled flow. In this manner, the cooling rate can be regulated by the flow rate and/or the temperature of the cooled tube.

Cooling is generally performed down to below the melting point of the crystalline form of the agrochemical active ingredients, preferably down to less than 50° C., especially preferably down to less than 30° C.

In general, the process according to the invention gives an aqueous suspension comprising at least 5% by weight, preferably at least 15% by weight and especially preferably at least 20% by weight of particles which comprise the agrochemical active ingredients in amorphous form, in each case based on the aqueous suspension. The particles prepared by the process according to the invention can be diluted or used as such. Furthermore, it is possible to concentrate or to dry the aqueous suspension, for example by spray drying. In a preferred embodiment, the aqueous suspension is used as a suspension. Here, the process according to the invention is performed without a drying step.

Further formulation auxiliaries may optionally be added to the melt, to the aqueous solution or to the aqueous suspension of the particles. Formulation auxiliaries are, for example, solvents, surfactants, inorganic emulsifiers (known as Pickering emulsifiers), antifoams, thickeners, antifreeze agents and bactericides. Formulations intended for seed dressing may additionally also comprise adhesives and, if appropriate, pigments.

Solvents can be added to the melt and/or to the aqueous solution and/or to the suspension of the particles. In general, water-soluble solvents will be added to the aqueous solution. The solubility in water is preferably at least 30 g/l, specifically at least 100 g/l water. The water-soluble solvent is usually added at a concentration of not more than 30% by weight, especially preferably not more than 10% by weight, in particular not more than 3% by weight and very specifically not more than 0.5% by weight, based on the amount of water. The antifreeze agents are not understood as meaning water-soluble solvents in the present context. In general, solvents which are insoluble in water will be added to the melt. The solubility in water is preferably not more than 100 g/l, specifically not more than 30 g/l water. Examples of suitable solvents are aromatics, aliphatics, fatty acid esters, fatty acid dialkyl amides or vegetable oils. The solvent which is insoluble in water will usually be added in a concentration of not more than 50% by weight, particularly preferably not more than 30% by weight, based on the total amount of agrochemical active ingredients. The abovementioned solvents which are soluble or insoluble in water may be added to the particle suspension in the abovementioned amounts.

In general, anionic, cationic and/or nonionic surfactants will be added. In the event that surfactant mixtures are used, the individual components will, naturally, have to be compatible with one another, which, if in doubt, can be verified by some preliminary experiments. In general, anionic emulsifiers are compatible with one another and with nonionic emulsifiers. The same also applies to cationic emulsifiers, while anionic and cationic emulsifiers are, in most cases, not compatible with one another.

Examples of customary nonionic surfactants are ethoxylated mono-, di- and trialkylphenols (degree of ethoxylation from 3 to 50, alkyl radical: $C_4$ to $C_{12}$) and ethoxylated fatty alcohols (degree of ethoxylation from 3 to 80; alkyl radical: $C_8$ to $C_{36}$). Examples are the Lutensol® A brands ($C_{12}$- to $C_{14}$-fatty alcohol ethoxylates, degree of ethoxylation from 3 to 8), Lutensol® AO brands ($C_{13}$- to $C_{15}$-oxoalcohol ethoxylates, degree of ethoxylation from 3 to 30), Lutensol® AT brands ($C_{16}$- to $C_{18}$-fatty alcohol ethoxylates, degree of ethoxylation from 11 to 80), Lutensol® ON brands ($C_{10}$-oxoalcohol ethoxylates, degree of ethoxylation from 3 to 11) and the Lutensol® TO brands ($C_{13}$-oxoalcohol ethoxylates, degree of ethoxylation from 3 to 20) from BASF SE. Others which are suitable are amphiphilic polymers, for example as described in EP 1 756 188 B1, paragraph [0012] to [0068], or in DE 10 2006 001 529 A1, paragraph [0025] to [0055], or those based on the monomers acrylic acid, butyl methacrylate, methyl methacrylate, hydroxyethyl methacrylate and/or iso-butyl methacrylate. Others which are suitable are amphiphilic block copolymers, in particular those based on ethylene oxide/propylene oxide. Examples are Pluronic® PE brands (EO-PO-EO tri-block copolymers; EO: ethylene oxide, PO: propylene oxide). Others which are suitable are comb polymers, especially those based on alkoxypolyoxyalkylene(meth)acrylates, such as comb polymers of methyl methacrylate, methacrylic acid and (methoxypolyethylene glycol)methacrylate (commercially available as Atlox® 4913 from Uniqema). Others which are customary are polysaccharides and their derivatives, preferably polysaccharides based on inulin, for example Inutec® SP1 (inulin from Chicoree with grafted-on alkyl groups).

Examples of customary anionic surfactants are alkali metal and ammonium salts of alkyl sulfates (alkyl radical: C8 to C12), for example sodium dodecyl sulfate, of sulfuric monoesters of ethoxylated alkanols (degree of ethoxylation from 4 to 30, alkyl radical: C12 to C18) and of ethoxylated alkylphenols (degree of ethoxylation from 3 to 50, alkyl radical: $C_4$ to $C_{12}$), of alkylsulfonic acids (alkyl radical: $C_{12}$ to $C_{18}$) and of alkylarylsulfonic acids (alkyl radical: $C_9$ to $C_{18}$). Other compounds which have proved to be further anionic surfactants are the compounds of the general formula (I)

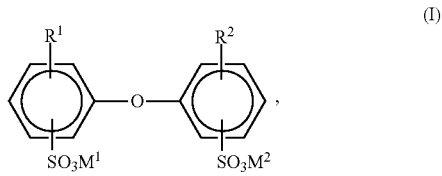

in which $R^1$ and $R^2$ are H atoms or $C_4$- to $C_{24}$-alkyl and are not simultaneously H atoms, and $M^1$ and $M^2$ can be alkali metal ions and/or ammonium ions. In the general formula (I), $R^1$ and $R^2$ are preferably linear or branched alkyl radicals having 6 to 18 C atoms, in particular having 6, 12 and 16 C atoms, or hydrogen, where $R^1$ and $R^2$ are not both simultaneously H atoms. $M^1$ and $M^2$ are preferably sodium, potassium or ammonium, with sodium being especially preferred. Especially advantageous are compounds (I) in which $M^1$ and $M^2$ are sodium, $R^1$ is a branched alkyl radical having 12 C atoms and $R^2$ is an H atom or $R^1$. Frequently, one uses technical mixtures with a content of from 50 to 90% by weight of the monoalkylated product, such as, for example, Dowfax® 2A1 (brand of Dow Chemical Company). Others which are suitable are salts of dialkylsulfosuccinates, such as sodium dioctylsulfosuccinate (commercially available as Lutensit® A-BO from BASF SE). Others which are suitable are arylphenol alkoxylates or their sulfated or phosphated derivatives, especially ethoxylated di- and tristyrylphenols or their sulfated or phosphated derivatives, such as Soprophor ® from Rhodia (ammonium salt of the ethoxylated tristyrylphenol sulfate with approximately 16 ethylene oxide groups per molecule). Likewise suitable are partially neutralized alkali metal salts of (meth)acrylic acid/maleic acid copolymers, for example the Sokalan® brands from BASF, in particular Sokalan CP45 (acrylic acid/maleic acid copolymer, sodium salt, partially neutralized).

Suitable cationic surfactants are, as a rule, cationic salts having a $C_6$- to C18-alkyl, -alkylaryl or heterocyclic radical, for example primary, secondary, tertiary or quaternary ammonium salts, alkanolammonium salts, pyridinium salts, imidazolinium salts, oxazolinium salts, morpholinium salts, thiazolinium salts and salts of amine oxides, quinolinium salts, isoquinolinium salts, tropylium salts, sulfonium salts and phosphonium salts. Examples which may be mentioned are dodecylammonium acetate or the corresponding sulfate, the sulfates or acetates of the various 2-(N,N,N-trimethylammonium)ethylparaffinic acid esters, N-cetylpyridinium sulfate, N-laurylpyridinium sulfate and N-cetyl-N,N,N-trimethylammonium sulfate, N-dodecyl-N,N,N-trimethylammonium sulfate, N-octyl-N,N,N-trimethylammonium sulfate, N,N-distearyl-N,N-dimethylammonium sulfate, and the Gemini surfactant N,N'-(lauryldimethyl)ethylenediamine disulfate, ethoxylated tallow fatty alkyl N-methylammonium sulfate and ethoxylated oleylamine (for example Uniperol® AC from BASF SE, approximately 12 ethylene oxide units). It is essential that the nucleophilicity of the anionic counter groups is as low as possible, for example perchlorate, sulfate, phosphate, nitrate and carboxylates such as acetate, trifluoroacetate, trichloroacetate, propionate, oxalate, citrate, benzoate, and conjugated anions of organosulfonic acids such as, for example, methylsulfonate, trifluoromethylsulfonate and para-toluenesulfonate, furthermore tetrafluoroborate, tetraphenylborate, tetrakis(pentafluorophenyl)borate, tetrakis[bis(3,5-trifluoromethyl)phenyl]borate, hexafluorophosphate, hexafluoroarsenate or hexafluoroantimonate.

The concentration of the added surfactant or its mixture can vary within wide ranges. It depends greatly on the active ingredient, or the active ingredient mixture, to be emulsified. It is usual to employ concentrations of from 0.1 to 30% by weight, based on the aqueous solution.

Examples of inorganic emulsifiers are metal salts such as salts, oxides and hydroxides of calcium, magnesium, iron, zinc, nickel, titanium, aluminum, silicon, barium or manganese. The following must be mentioned: magnesium hydroxide, magnesium carbonate, magnesium oxide, calcium oxalate, calcium carbonate, barium carbonate, barium sulfate, titanium dioxide, aluminum oxide, aluminum hydroxide and zinc sulfide. Silicates, bentonite, hydroxyapatite and hydrotalcites may also be mentioned.

Examples of thickeners (compounds which impart a pseudo-plastic rheology to the formulation, i.e. high viscosity at rest but low viscosity when agitated) are, for example, polysaccharides such as xanthan gum, or organic layer minerals.

Examples of suitable antifoams are silicone emulsions, long-chain alcohols, fatty acids, organofluorine compounds and their mixtures.

Bactericides may be added to stabilize the aqueous formulation. Suitable bactericides which may be present in the formulations according to the invention are all those bactericides which are conventionally used in the formulation of agrochemical active ingredients such as, for example, dichlorophen and benzyl alcohol hemiformal.

Examples of suitable antifreeze agents are polyhydric alcohols such as ethylene glycol, propylene glycol or glycerol, preferably glycerol. Usually, 0 to 30% by weight, preferably 10 to 20% by weight, based on the aqueous solution, are added.

Suitable adhesives which may be present in seed-dressing formulations are all customary binders which can be employed in seed-dressing products. The following may be mentioned by preference: polyvinylpyrrolidone, polyvinyl acetate, polyvinyl alcohol and tylose. In a preferred embodiment, less than 5% by weight, preferably less than 1% by weight, very especially less than 0.1% by weight and in particular no polyvinyl alcohol is/are added to the process according to the invention or to the particles according to the invention.

Furthermore, colorants may also optionally be added to the formulations according to the invention. In this context, colorants which are suitable are all those conventionally used for such purposes, for example C.I. Pigment Red 48:2. Both pigments, which are sparingly soluble in water, and dyes, which are soluble in water, may be employed in this context.

In general, it is not necessary to add crystallization inhibitors which do not take the form of agrochemical active ingredients. No crystallization inhibitors need to be added in particular to the melt comprising the two agrochemical active ingredients. It is preferred to add not more than 5% by weight, especially preferably not more than 1% by weight and specifically no crystallization inhibitors which do not take the form of agrochemical active ingredients. In a preferred embodiment, not more than 5% by weight, preferably not more than 1% by weight and specifically no polymeric crystallization inhibitors are added. Here, the % by weight of the crystallization inhibitor relate in each case to the total amount of agrochemical active ingredient. In this context, "polymeric" is understood as meaning compounds with at least three recurring monomer units and a molar mass of at least 800 g/mol, in particular at least 2000 g/mol. An example of such polymeric crystallization inhibitors is the copolymer mentioned in WO 2006/111327, comprising a monoethylenically unsaturated monomer which has at least one sulfonic acid group. In a further preferred embodiment, not more than 5% by weight, especially preferably not more than 1% by weight, and specifically no copolymer comprising a monoethylenically unsaturated monomer which has at least one sulfonic acid group is/are added to the melt comprising the two agrochemical active ingredients.

The process according to the invention usually gives particles which are free from a polymeric coating. In particular, the process gives particles which are free from a coating comprising polyvinyl alcohol. Therefore, the process usually does not comprise any step for coating the particles with a polymer. For example, the process does not comprise any addition of an aqueous polymer solution, such as polyvinyl alcohol, and subsequent spray drying.

The invention furthermore relates to the use of an agrochemical active ingredient for inhibiting the crystallization of another agrochemical active ingredient in a preparation process for particles which comprise both agrochemical active ingredients in amorphous form, where a melt comprising the two molten agrochemical active ingredients is emulsified in an aqueous solution and cooled. Suitable embodiments of the preparation process and of the agrochemical active ingredients are described as hereinabove. Preferred is at least one of the agrochemical active ingredients metconazole, pyraclostrobin, epoxiconazole or prochloraz, in particular pyraclostrobin, epoxiconazole or prochloraz. In a further embodiment, the active ingredients are metconazole, pyraclostrobin, epoxiconazole, prochloraz, triticonazole, boscalid, N-(3',4', 5'-trifluorobiphenyl-2-yl)-3-difluoromethyl-1-methyl-1H-pyrazole-4-carboxamide or metalaxyl are suitable. Especially preferred are the two agrochemical active ingredients pyraclostrobin and epoxiconazole, or pyraclostrobin and prochloraz. In a further embodiment, the two agrochemical active ingredients are especially preferably pyraclostrobin and prochloraz, prochloraz and triticonazole, pyraclostrobin and metconazole, pyraclostrobin and boscalid, pyraclostrobin and metalaxyl, triticonazole and epoxiconazole, triticonazole and metalaxyl, epoxiconazole and metconazole, epoxiconazole and boscalid, N-(3',4',5'-trifluorobiphenyl-2-yl)-3-difluoromethyl-1-methyl-1H-pyrazole-4-carboxamide and triticonazole, N-(3',4',5'-trifluorobiphenyl-2-yl)-3-difluoromethyl-1-methyl-1H-pyrazole-4-carboxamide and metconazole, or pyraclostrobin, metalaxyl and triticonazole. The crystallization-inhibitory agrochemical active ingredient is generally present in a concentration of in each case at least 5% by weight, preferably at least 10% by weight, based on the total amount of active ingredient. In most cases, the particles will comprise no more than 5% by weight of polymeric crystallization inhibitors based on the total amount of the agrochemical active ingredients.

The invention furthermore relates to particles which comprise two agrochemical active ingredients in amorphous form and which are obtainable by the process according to the invention, where at least one of the agrochemical active ingredients is metconazole, pyraclostrobin, epoxiconazole or prochloraz. In a further embodiment, at least one of the agrochemical active ingredients is metconazole, pyraclostrobin, epoxiconazole, prochloraz, triticonazole, boscalid, N-(3',4', 5'-trifluorobiphenyl-2-yl)-3-difluoromethyl-1-methyl-1H-pyrazole-4-carboxamide or metalaxyl. Suitable embodiments of the preparation process, of the particles and of the agrochemical active ingredients are described as hereinabove. Preferred are the agrochemical active ingredients pyraclostrobin and epoxiconazole or pyraclostrobin and prochloraz. Preferably, pyraclostrobin and epoxiconazole are present in a weight ratio of from 5:95 to 95:5, in particular 10:90 to 90:10 and specifically 50:50 to 90:10, or pyraclostrobin and prochloraz in a weight ratio of from 5:95 to 95:5, in particular 10:90 to 90:10 and specifically 50:50 to 70:30.

The invention furthermore relates to particles which comprise two agrochemical active ingredients in amorphous form, where the two agrochemical active ingredients are pyraclostrobin and epoxiconazole, or pyraclostrobin and prochloraz. Suitable embodiments of the preparation process, of the particles and of the agrochemical active ingredients are described as hereinabove. Preferably, pyraclostrobin and epoxiconazole are present in a weight ratio of from 5:95 to 95:5, in particular 10:90 to 90:10 and specifically 50:50 to 90:10, or pyraclostrobin and prochloraz in a weight ratio of from 5:95 to 95:5, in particular 10:90 to 90:10 and specifically 50:50 to 70:30. The abovementioned particles can be obtained for example by the process according to the invention. In a further embodiment, the two agrochemical active ingredients are pyraclostrobin and prochloraz, prochloraz and triticonazole, pyraclostrobin and metconazole, pyraclostrobin and boscalid, pyraclostrobin and metalaxyl, triticonazole and epoxiconazole, triticonazole and metalaxyl, epoxiconazole and metconazole, epoxiconazole and boscalid, N-(3',4',5'-trifluorobiphenyl-2-yl)-3-difluoromethyl-1-methyl-1H-pyrazole-4-carboxamide and triticonazole, N-(3',4', 5'-trifluorobiphenyl-2-yl)-3-difluoromethyl-1-methyl-1H-pyrazole-4-carboxamide and metconazole, or pyraclostrobin, metalaxyl and triticonazole. Especially preferably, the two agrochemical active ingredients are pyraclostrobin and prochloraz, prochloraz and triticonazole, or pyraclostrobin and metalaxyl. In most cases, the particles will comprise no more than 5% by weight of polymeric crystallization inhibitors based on the total amount of the agrochemical active ingredients. A further embodiment includes particles which comprise two agrochemical active ingredients in amorphous form, the two agrochemical active ingredients being pyraclostrobin and epoxiconazole, and the particles comprising no more than 5% by weight of polymeric crystallization inhibitors, based on the total amount of the agrochemical active ingredients.

A further subject matter relates to an agrochemical formulation comprising the particles prepared by the process according to the invention or the particles according to the invention, and optionally further formulation auxiliaries. Suitable embodiments of the preparation process, of the formulation auxiliaries, of the particles and of the agrochemical active ingredients are as described above. Preferably, the agrochemical formulation is a suspension (suspension concentrate SC, oil dispersion OD, flowable concentrate for seed treatment FS), a suspoemulsion (SE), granules (granules GR, fine granules FG, macrogranules GG, microgranules MG), a dust (dustable powder DP, powder for seed treatment DS) or a water-dispersible powder (wettable powder WP, water-soluble powder SP, water-soluble powder for seed treatment SS, water-dispersible powder for seed treatment with slurry WS) especially preferably a suspension or a suspoemulsion and specifically a suspension.

For use, the agrochemical formulation can be diluted with water, other customary liquids or their aqueous mixtures. The dilution and the application rate will depend on a variety of factors, such as the type of machine employed, the method and the frequency of the desired application. It may be desirable to introduce into the spray tank one or more formulation auxiliaries. Likewise, the agrochemical formulation may be mixed with fertilizers before being applied. The agrochemical formulation may be employed as the only pesticide or together with other pesticides such as microbicides, fungicides, herbicides, insecticides, acaricides and the like.

The present invention furthermore claims a method of controlling phytopathogenic fungi and/or undesirable vegetation and/or undesirable attack by insects or mites and/or for regulating plant growth, wherein an agrochemical formulation according to the invention is allowed to act on the respective pests (i.e. phytopathogenic fungi and/or undesirable insects or mites), their environment or the plants to be protected from the respective pests, or the soil, and/or on undesirable plants and/or the useful plants and/or their environment.

The present invention also claims a method of controlling undesirable attack by insects or mites on plants and/or of controlling phytopathogenic fungi and/or for controlling undesirable vegetation, where seeds of useful plants are treated with an agrochemical formulation according to the invention.

The agrochemical formulation according to the invention can be used for the treatment, preferably the dressing, of seed. This term comprises all seed-treatment techniques known to the skilled worker (for example seed dressing, seed coating and pelleting). When the seed has been treated or dressed with the, agrochemical formulation, this means that the agrochemical formulation adheres to the surface of the seed or has penetrated into the seed. The term seed comprises any type of seed, such as, for example, grains, seeds, fruits, tubers, cuts and similar forms. However, the seed employed may also be the seed of transgenic plants, or of plants which have been obtained by conventional growing methods. In this context, the term seed preferably describes grains and seeds.

The particles according to the invention have a high active ingredient content, are storage stable, in particular in the form of suspensions (for example, virtually no crystals form during storage), they have a high biological activity and very good bioavailability. The preparation process according to the invention makes possible the preparation of these advantageous particles. It allows the emulsification of higher-melting active ingredient(s) at temperatures which are markedly below the melting point/melting range of the higher-melting active ingredient(s) in the form of the pure substance(s). This has the first advantage that the active ingredient is subjected to less thermal stress, which means the risk of product damage is reduced. Secondly, less energy has to be expended for heating the active ingredient and for cooling the fine emulsion. A further advantage is that the suspension of active ingredients is stable without a complicated drying step being necessary. Another advantage is that the preparation process and the particles manage without the addition of polymeric crystallization inhibitors or polymeric coating layers which are expensive or complicated to synthesize.

The examples which follow illustrate the invention without limiting it.

EXAMPLES

Materials

Emulsifier 1: aqueous dispersion of an amphiphilic copolymer of the monomers acrylic acid, butyl methacrylate, methyl methacrylate, hydroxyethyl methacrylate and isobutyl methacrylate with a solids content of 33% by weight and a polymer particle size of approximately 10 to 60 nanometers.

Emulsifier 2: sodium dodecyl sulfate (SDS)

Emulsifier 3: poly(ethylene glycol block propylene glycol block ethylene glycol), where the propylene glycol block has a molar mass of 3250 g/mol and the polymer a mass of approximately 6500 g/mol (commercially available, for example as Pluronic® PE 10500)

Emulsifier 4: nonionic emulsifier based on inulin from chicory with grafted-on lauryl groups (commercially available, for example as Inutec® SP1).

Emulsifier 5: sodium dioctylsulfosuccinate, 60% strength solution in a water/neopentyl glycol mixture (commercially available, for example as Lutensit® A-BO)

Emulsifier 6: comb polymer of methyl methacrylate, methacrylic acid and (methoxypolyethylene glycol)methacrylate, 33% solution in 1:1 mixture propylene glycol/water (commercially available, for example as Atlox® 4913 from Uniqema).

Emulsifier 7: ethoxylated tristyrylphenol sulfate (ammonium salt with approximately 16 ethylene oxide groups per molecule; melting point of approx. 15° C.; commercially available, for example as Soprophor® 4D384 from Rhodia).

Emulsifier 8: acrylic acid/maleic acid copolymer, sodium salt, partially neutralized (mean molar mass 70 000 g/mol; K value 60 determined as specified in DIN ISO 1628-1 at 1% dry matter in distilled water, pH 7; commercially available, for example as Sokalan CP45 from BASF).

Emulsifier 9: sodium salt of a phenolsulfonic acid/formaldehyde condensate (commercially available as Wettol® D1 from BASF).

Emulsifier 10: a lauryl-carbamate-substituted inulin which has been prepared by reacting an isocyanate with inulin in the presence of a basic catalyst (commercially available as Inutec® SP1 from Orafti, Ghent or NRC Nordmann, Rassmann).

Pyraclostrobin: m.p. 64-65° C., solubility in water at 20° C.: 1.9 mg/l

Epoxiconazole: m.p. 136° C., solubility in water at 20° C.: 66 mg/l

Prochloraz: m.p. 47-49° C., solubility in water at 25° C.: 34 mg/l

Metalaxyl: m.p. 64-72° C., solubility in water at 22° C.: 8.4 g/l

Triticonazole: m.p. 139-141° C., solubility in water at 20° C.: 9 mg/l

Metconazole: m.p. 100-108° C., solubility in water at 20° C.: 30 mg/l

Boscalid: m.p. 143-144° C., solubility in water at 20° C.: 5 mg/l

Fungicide A: N-(3',4',5'-trifluorobiphenyl-2-yl)-3-difluoromethyl-1-methyl-1H-pyrazole-4-carboxamide, m.p. 155-158° C., can be prepared as described in WO2009/007344.

Example 1A

Crystallization-Inhibiting Active Ingredient Mixture a) Mixture Pyraclostrobin and Epoxiconazole In an experimental series, the weight ratio of pyraclostrobin and epoxiconazole was varied from 5:7, 3:7 and 3:8. To this end, the pulverulent active ingredients were mixed with one another and converted into a homogeneous melt by warming above the melting point of the mixture of 80-90° C., with stirring. The melt was left to cool at 20° C. After the melt had cooled to 20° C., a light microscope was used to ascertain whether the melt was homogeneous or contained crystals. One hour after cooling, the mixture of 5 parts by weight of pyraclostrobin and 7 parts by weight of epoxiconazole (corresponding to a ratio of 42:58) comprised crystals. One hour after cooling, the mixture of 8 parts of pyralostrobin and 3 parts of epoxiconazole (corresponding to a ratio of 73:27) did not contain any crystals.

b) Mixture Prochloraz and Pyraclostrobin

The weight ratio of pulverulent pyraclostrobin and of prochloraz which had been reduced to a powder in a mortar was varied from 1:9 to 9:1. To this end, the two active ingredients were mixed and molten at 70° C. The sample was homogenized by careful shaking, and a sample was taken. 1 h after cooling, the samples in the range prochloraz/pyraclostrobin 9:1 to 1:9 had not crystallized, as ascertained by DSC measurement. After 6 days, the sample with the weight ratio 9:1 was fully crystallized, while the other samples were crystallized to some extent only, or not at all.

Example 1B

Crystallization-Inhibiting Active Ingredient Mixtures

The active ingredients were dissolved in acetone (see Table 1) and combined to give the mixing ratios (Table 2). The acetone was evaporated for two days at room temperature and then stripped off in vacuum for 5 h at 80° C. (method A). Temperature-insensitive active ingredients Were subsequently melted for an additional 15 h at 140° C. (method B). The samples were cooled to 20° C. in each case and stored for one week at 20° C. The samples remained clear and translucent (i.e. amorphous) and revealed no crystals.

TABLE 1

| Active ingredient | Content (%) |
|---|---|
| Prochloraz | 50 |
| Pyraclostrobin | 50 |
| Triticonazole | 10 |
| Epoxiconazole | 15 |
| Metconazole | 30 |
| Boscalid | 10 |
| Fungicide A | 30 |
| Metalaxyl | 50 |

TABLE 2

| Active ingredient 1 | Active ingredient 2 | Weight ratio | Storage | Crystal formation |
|---|---|---|---|---|
| Triticonazole | — | 100 | B | Yes |
| Epoxiconazole | — | 100 | B | Yes |
| Boscalid | — | 100 | B | Yes |
| Fungicide A | — | 100 | B | Yes |
| Metalaxyl | — | 100 | A | Yes |
| Prochloraz | Triticonazole | 80:20 | A | No |
| Pyraclostrobin | Metconazole | 80:20 | A | No |
| Pyraclostrobin | Metconazole | 60:40 | A | No |
| Pyraclostrobin | Metconazole | 40:60 | A | No |
| Pyraclostrobin | Boscalid | 80:20 | A | No |
| Pyraclostrobin | Metalaxyl | 80:20 | A | No |
| Pyraclostrobin | Metalaxyl | 60:40 | A | No |
| Pyraclostrobin | Metalaxyl | 40:60 | A | No |
| Pyraclostrobin | Metalaxyl + Triticonazole | 20:60:20[a] | A | No |
| Triticonazole | Epoxiconazole | 60:40 | B | No |
| Triticonazole | Epoxiconazole | 40:60 | B | No |
| Triticonazole | Fungicide A | 60:40 | B | No |
| Triticonazole | Metalaxyl | 20:80 | B | No |
| Epoxiconazole | Metconazole | 40:60 | B | No |
| Epoxiconazole | Metconazole | 20:80 | B | No |
| Epoxiconazole | Boscalid | 40:60 | B | No |
| Metconazole | Fungicide A | 80:20 | B | No |
| Metconazole | Fungicide A | 60:40 | B | No |

[a]Mixture of 20:60:20 of pyraclostrobin:metalaxyl:triticonazole

Example 2

Active Ingredient Mixture Pyraclostrobin and Epoxiconazole

In a stirred vessel, 8 parts by weight of pulverulent pyraclostrobin and 3 parts by weight of pulverulent epoxiconazole were heated at temperatures of from 80 to 90° C. and molten in the process. The mixture was stirred until a transparent monophasic liquid was present. In a second vessel, the continuous phase consisting of 59 parts of water and 30 parts of emulsifier 1, was prepared and also heated to 80 to 90° C. At this point in time, the molten mixture was placed into the continuous phase and incorporated in the form of a dispersion with the aid of a stirring means of the Ultraturrax® T 25 type, level 6, 24000 revolutions per minute, dispersing time 2 minutes. The crude emulsion prepared in this manner was processed in a high-pressure homogenizer (high-pressure pump G 400, Maximator GmbH, D-99734 Nordhausen) at a temperature of approximately 85° C. and a homogenization pressure of 2000 bar. This gave a fine emulsion which directly after the homogenization process was cooled with stirring in an ice-water bath to temperatures of 20° C. or less at a cooling rate of 3.0 K/min.

Typical characteristics of the particle size distribution were determined by means of laser light diffraction and are:
$x_{10}=0.413$ μm
$x_{50}=0.851$ μm
$x_{90}=1.701$ μm
$x_{3,2}=0.736$ μm.

To determine the particle size distribution of the eleven-percent strength formulation of epoxiconazole and pyraclostrobin, a Mastersizer 2000 laser diffraction spectrometer from Malvern Instruments GmbH (Herrenberg, Germany) was employed. To carry out the measurements, 1.5 ml of the original suspension were stirred into 50 ml of fully demineralized water, using a magnetic stirrer. 3 ml were taken from this dilute sample and added to 125 ml of fully demineralized water in the Hydro S cell of the instrument at a stirrer speed of 250 revolutions per minute. The sample of the active ingredient suspension and the fully demineralized water used for the dilution were at room temperature.

To analyze the mixture for crystalline components, a sample was analyzed by X-ray powder diffractometry (XRD). To this end, the sample was placed into a sample holder, covered with Styroflex film and analyzed in a diffractometer D 5000 (at 25° C.; step size 0.020°; step time 4.8 s; Cu anode). As demonstrated by the X-ray diffractogram in FIG. 1, the sample was amorphous as determined by X-ray analysis. The signals A were those of the Styroflex film.

Example 3

Active Ingredient Mixture Pyraclostrobin and Epoxiconazole

In a stirred vessel, 8 parts by weight of pulverulent pyraclostrobin and 3 parts by weight of pulverulent epoxiconazole were heated at temperatures of from 80 to 90° C. and molten in the process. The mixture was stirred until a transparent monophasic liquid was present. In a second vessel, the continuous phase consisting of 84.5 parts by weight of water and 3 parts by weight of emulsifier 2 and 1.5 parts by weight of emulsifier 3, was prepared and also heated to 80 to 90° C. At this point in time, the molten mixture was placed into the continuous phase and incorporated in the form of a dispersion with the aid of a stirring means of the Ultraturrax® T 25 type, level 6, 24000 revolutions per minute, dispersing time 2 minutes. The crude emulsion prepared in this manner was processed in a high-pressure homogenizer (high-pressure pump G 400, Maximator GmbH, D-99734 Nordhausen) at a temperature of approximately 85° C. and a homogenization pressure of 2000 bar. This gave a fine emulsion which directly after the homogenization process was cooled with stirring in an ice-water bath to temperatures of 20° C. or less at a cooling rate of 3.0 K/min.

Typical characteristics of the particle size distribution were determined by means of laser light diffraction (measured using a Malvern Mastersizer 2000, method: see Example 2) and are:
$x_{10}=0.525$ μm
$x_{50}=1.000$ μm
$x_{90}=1.852$ μm
$x_{3,2}=0.888$ μm Example 4

Active Ingredient Mixture Pyraclostrobin and Epoxiconazole

In a stirred vessel, 8 parts of pulverulent pyraclostrobin and 3 parts of pulverulent epoxiconazole were heated at temperatures of from 80 to 90° C. and molten in the process. The mixture was stirred until a transparent monophasic liquid is present. In a second vessel, the continuous phase consisting of 81.5 parts of water and 3 parts of emulsifier 2, 3 parts of emulsifier 4 and 1.5 parts of emulsifier 3, was prepared and also heated to 80 to 90° C. At this point in time, the molten mixture was placed into the continuous phase and incorporated in the form of a dispersion with the aid of a stirring means of the Ultraturrax® T 25 type, level 6, 24000 revolutions per minute, dispersing time 2 minutes. The crude emulsion prepared in this manner was processed in a high-pressure homogenizer (high-pressure pump G 400, Maximator GmbH, D-99734 Nordhausen) at a temperature of approximately 85° C. and a homogenization pressure of 2000 bar. This gave a fine emulsion which directly after the homogenization process was cooled with stirring in an ice-water bath to temperatures of 20° C. or less at a cooling rate of 3.0 K/min.

Typical characteristics of the particle size distribution were determined by means of laser light diffraction (measured using a Malvern Mastersizer 2000, method: see Example 2) and are:
$x_{10}$=0.356 µm
$x_{50}$=0.831 µm
$x_{90}$=2.378 µm
$x_{3,2}$=0.701 µm

Example 5

Active Ingredient Mixture Prochloraz and Pyraclostrobin

A melt of 4 parts by weight of prochloraz and one part by weight of pyraclostrobin was prepared at 65° C. and emulsified at a concentration of 20% by weight in a water/glycerol mixture (85/15) in the presence of an emulsifier mixture, using an ultrasonic processor (30 s at 65° C., 100% power, energy supply 400 W/ml). After the emulsion had cooled to room temperature, a suspension of amorphous particles was obtained, the active ingredient content being 20% by weight based on the suspension.

The following emulsifier mixtures were employed (in each case % by weight based on the total batch):
Batch A) 4% by weight of emulsifier 5 and emulsifier 6 in the weight ratio of 3/1
Batch B) 20% by weight of emulsifier 1
Batch C) 6% by weight of emulsifier 8

All three batches gave suspensions which were stable for at least seven weeks. The suspension was assessed visually immediately after the preparation. The particle size distribution was determined after 4 weeks' storage.

| Batch | Visual assessment | Particle size distribution [µm] | | | |
|---|---|---|---|---|---|
| | | d10 | d50 | d90 | mean |
| A | homogeneous | 0.98 | 1.69 | 6.37 | 2.65 |
| B | homogeneous | 0.07 | 0.09 | 1.44 | 0.53 |
| C | homogeneous | 0.66 | 1.53 | 4.86 | 2.14 |

Example 6

Active Ingredient Mixture Prochloraz and Pyraclostrobin

The melt emulsification was repeated as in Example 5, using emulsifier b), the concentration of the active ingredient mixture and of the emulsifier being varied as follows:

| Batch | A | B | C | D | E |
|---|---|---|---|---|---|
| Concentration of emulsifier b) [% by weight] | 20 | 20 | 20 | 10 | 6 |
| Concentration of active ingredient mixture [% by weight] | 20 | 10 | 6 | 20 | 20 |

The particle sizes were not capable of being measured using static light scattering, and were less than 1 µm immediately after the preparation. The dispersions prepared were increasingly opaque with decreasing active ingredient/dispersant ratios. The samples with 20% by weight of active ingredient were milky-white and sedimented after three weeks at the most. All samples were still stable after more than 10 weeks' storage at room temperature, and, while sedimented, redispersible. No substantial particle growth was observed, and no crystals were discernible under the microscope.

Example 7

Pyraclostrobin (Comparative Experiment; Not According to the Invention)

The melt emulsification was repeated as in Example 6, using emulsifier b), but only pure pyraclostrobin was used instead of the active ingredient mixture. The concentration of pyraclostrobin and of the emulsifier was varied as follows:

| Batch | A | B | C |
|---|---|---|---|
| Concentration of emulsifier b) [% by weight] | 20 | 20 | 20 |
| Concentration of active ingredient [% by weight] | 20 | 10 | 6 |

The samples had sedimented after only one day and were no longer redispersible. Crystals were discernible even with the naked eye.

Example 8

Active Ingredient Mixture Pyraclostrobin and Prochloraz 80 g of prochloraz, 20 g of pyraclostrobin, 15 g of emulsifier 5, 5 g of emulsifier 6, 57 g of glycerol, 50 g of a 2% by weight strength aqueous solution of xanthan and 273 g of water were heated at 65° C., with stirring. The crude emulsion with the molten active ingredients was subjected to shearing at 15000 rpm, using an inline dissolver (Megatron MT 3000 from Kinematica AG). After 30 min, the particle size in the fine emulsion was analyzed using a Malvern Mastersizer 2000 ($x_{90}$=1.7 µm) and the emulsion was then cooled in an ice-bath with gentle stirring. This gave rise to a suspension of solid, amorphous particles.

Wet-screening over a 150 µm screen gave no residue. The sample was stable over 4 weeks. No significant particle size growth was observed.

Example 9

Active Ingredient Mixture Pyraclostrobin and Prochloraz

The method of Example 8 was repeated, except that, instead of the inline dissolver, an Ultraturrax (Polytron PT 4000 from Kinematica AG) was used for 30 min at 15000 rpm for the shearing. This gave a particle size of $x_{90}=1.6$ µm. The sample was stable over 4 weeks. No significant particle size growth was observed.

Example 10

Active Ingredient Mixture Pyraclostrobin and Prochloraz

The method of Example 8 was repeated, except that, instead of the inline dissolver, an Ultraturrax (Polytron PT 4000 from Kinematica AG) was used for 10 min at 15000 rpm for the shearing and, instead of emulsifier 5, emulsifier 7 in the same amount. This gave a particle size of $x_{90}=3.0$ µm. The sample was stable over 4 weeks. No significant particle size growth was observed.

Example 11

Active Ingredient Mixture Pyraclostrobin and Prochloraz

The method of Example 8 was repeated, except that, instead of the inline dissolver, an Ultraturrax (Polytron PT 4000 from Kinematica AG) was used for 10 min at 15000 rpm for the shearing and, instead of emulsifier 6, emulsifier 3 in the same amount. This gave a particle size of $x_{90}=1.5$ µm. The sample was stable over 4 weeks. No significant particle size growth was observed.

Example 12

Active Ingredient Mixture Pyraclostrobin and Metalaxyl

The method was carried out as described in Example 2. The active ingredient mixture consisted of 6 parts by weight of pyraclostrobin and 4 parts by weight of metalaxyl. The emulsification was carried out using 60 parts by weight of water and 30 parts by weight of emulsifier 1. The particle size distribution was $x_{10}=0.337$ µm, $x_{50}=0.793$ µm and $x_{90}=1.726$ µm. After storage for four days, the data were $x_{10}=0.369$ µm, $x_{50}=0.720$ µm and $x_{90}=1.385$ µm. No crystals were observed under the light microscope.

Example 13

Active Ingredient Mixture Pyraclostrobin and Metalaxyl

The method was carried out as described in Example 2. The active ingredient mixture consisted of 6 parts by weight of pyraclostrobin and 4 parts by weight of metalaxyl. The emulsification was carried out using 80 parts by weight of water and 10 parts by weight of emulsifier 9. The particle size distribution was $x_{10}=0.364$ µm, $x_{50}=0.821$ µm and $x_{90}=1.890$ µm. After storage for two days, the data were $x_{10}=0.441$ µm, $x_{50}=1.035$ µm and $x_{90}=2.676$ µm. No crystals were observed under the light microscope.

Example 14

Active Ingredient Mixture Prochloraz and Triticonazole

The method was carried out as described in Example 2. The active ingredient mixture consisted of 8 parts by weight of prochloraz and 2 parts by weight of triticonazole. The emulsification was carried out using a continuous phase of 59 parts by weight of water, 30 parts by weight of dipotassium hydrogen phosphate and 1 part by weight of emulsifier 10 (the emulsifier being incorporated into the aqueous dipotassium hydrogen phosphate solution with an Ultraturrax, resulting in a dispersion). The particle size distribution was $x_{10}=0.349$ µm, $x_{50}=0.935$ µm and $x_{90}=4.866$ µm. After storage for 24 h, the data were $x_{10}=0.360$ µm, $x_{50}=945$ µm and $x_{90}=4.508$ µm. No crystals were observed under the light microscope.

The invention claimed is:

1. A process for the preparation of particles which comprise two agrochemical active ingredients in amorphous form, wherein a melt comprising the two agrochemical active ingredients, which are molten, is emulsified in an aqueous solution and cooled,
   wherein one agrochemical active ingredient inhibits crystallization of the other agrochemical active ingredient,
   wherein not more than 5% by weight of polymeric crystallization inhibitors, based on the total amount of the agrochemical active ingredients, are added to the melt,
   wherein the two agrochemical ingredients have a melting point of at least 40° C. and a solubility in water of not more than 1% by weight at 20° C.,
   wherein at least one of the agrochemical ingredients has a melting point of not more than 170° C. and
   wherein the particles are in amorphous form.

2. The process according to claim 1, wherein the particles are unencapsulated.

3. The process according to claim 1, wherein the crystallization-inhibiting activity of the one agrochemical active ingredient on the other agrochemical active ingredient is determined by
   a) mixing the active ingredients with each other, converting them into a homogeneous melt by heating above the melting point of the mixture, and allowing the melt to cool, or
   b) dissolving the active ingredients separately in a solvent, mixing the active-ingredient-comprising solutions and subsequently removing the solvent;
   and, subsequently determining with the aid of a light microscope or dynamic differential scanning calorimetry (DSC) whether the solidified melt or the dried mixture comprises crystals.

4. The process according to claim 1, wherein at least one of the agrochemical active ingredients is metconazole, pyraclostrobin, epoxiconazole, prochloraz, triticonazole, boscalid, N-(3',4',5'-trifluorobiphenyl-2-yl)-3-difluoromethyl-1-methyl-1H-pyrazole-4-carboxamide or metalaxyl.

5. A particle which comprises two agrochemical active ingredients in amorphous form, wherein the two agrochemical active ingredients are pyraclostrobin and prochloraz, prochloraz and triticonazole, pyraclostrobin and metconazole, pyraclostrobin and boscalid, pyraclostrobin and metalaxyl, triticonazole and epoxiconazole, triticonazole and metalaxyl, epoxiconazole and metconazole, epoxiconazole and boscalid, N-(3', 4'-trifluorobiphenyl-2-yl)-3-difluoromethyl- 1-methyl-1H-pyrazole-4-carboxamide and triticonazole, N-(3',4',5'-trifluorobiphenyl-2-yl)-3-difluoromethyl-1-methyl-1H-pyrazole-4-carboxamide and metconazole, or pyraclostrobin, metalaxyl and triticonazole.

6. The particle according to claim 5, wherein the two agrochemical active ingredients are pyraclostrobin and prochloraz, prochloraz and triticonazole or pyraclostrobin and metalaxyl.

7. The particle according to claim 5, which comprises not more than 5% by weight of polymeric crystallization inhibitors, based on the total amount of the agrochemical active ingredients.

8. A particle which comprises two agrochemical active ingredients in amorphous form, wherein the two agrochemical active ingredients are pyraclostrobin and epoxiconazole and the particle comprises not more than 5% by weight of polymeric crystallization inhibitors, based on the total amount of the agrochemical active ingredients.

9. An agrochemical formulation comprising the particles prepared as described in claim 1 and optionally further formulation auxiliaries.

10. A method of controlling phytopathogenic fungi and/or undesirable vegetation and/or undesirable attack by insects or mites and/or for regulating plant growth, wherein an agrochemical formulation according to claim 9 is allowed to act on the respective pests, their environment or the plants to be protected from the respective pests, or the soil, and/or on undesirable plants and/or the useful plants and/or their environment.

11. A method of controlling undesirable attack by insects or mites on plants and/or of controlling phytopathogenic fungi and/or of controlling undesirable vegetation, wherein seeds of useful plants are treated with an agrochemical formulation according to claim 9.

12. Seeds dressed with an agrochemical formulation according to claim 9, where the formulation adheres to the surface of the seed or has penetrated into the seed.

13. The method according to claim 10, wherein at least one of the agrochemical active ingredients is metconazole, pyraclostrobin, epoxiconazole, prochloraz, triticonazole, boscalid, N-(3',4',5'-trifluorobiphenyl-2- yl)-3-difluoromethyl-1-methyl-1H-pyrazole-4-carboxamide or metalaxyl.

14. The method according to claim 10, wherein the particle comprises two agrochemical active ingredients in amorphous form, wherein the two agrochemical active ingredients are pyraclostrobin and prochloraz, prochloraz and triticonazole, pyraclostrobin and metconazole, pyraclostrobin and boscalid, pyraclostrobin and metalaxyl, triticonazole and epoxiconazole, triticonazole and metalaxyl, epoxiconazole and metconazole, epoxiconazole and boscalid, N-(3',4',4',5'-trifluorobiphenyl-2-yl)-3-difluoromethyl-1-methyl-1H-pyrazole-4-carboxamide and triticonazole, N-(3',4',5'-trifluorobiphenyl-2-yl)-3-difluoromethyl-1-methyl-1H-pyrazole-4-carboxamide and metconazole, or pyraclostrobin, metalaxyl and triticonazole.

15. The method according to claim 10, wherein the two agrochemical active ingredients are pyraclostrobin and prochloraz, prochloraz and triticonazole or pyraclostrobin and metalaxyl.

16. The method according to claim 11, wherein at least one of the agrochemical active ingredients is metconazole, pyraclostrobin, epoxiconazole, prochloraz, triticonazole, boscalid, N-(3',4',5'-trifluorobiphenyl-2-yl)-3-difluoromethyl-1-methyl-1H-pyrazole-4-carboxamide or metalaxyl.

17. The method according to claim 11, wherein the particle comprises two agrochemical active ingredients in amorphous form, wherein the two agrochemical active ingredients are pyraclostrobin and prochloraz, prochloraz and triticonazole, pyraclostrobin and metconazole, pyraclostrobin and boscalid, pyraclostrobin and metalaxyl, triticonazole and epoxiconazole, triticonazole and metalaxyl, epoxiconazole and metconazole, epoxiconazole and boscalid, N-(3',4',5'-trifluorobiphenyl-2-yl)-3-difluoromethyl-1-methyl-1H-pyrazole-4-carboxamide and triticonazole, N-(3', 4', 5'-trifluorobiphenyl- 2yl-3-difluoromethyl-1-methyl-1H-pyrazole-4-carboxamide and metconazole, or pyraclostrobin, metalaxyl and triticonazole.

18. The method according to claim 11, wherein the two agrochemical active ingredients are pyraclostrobin and prochloraz, prochloraz and triticonazole or pyraclostrobin and metalaxyl.

* * * * *

UNITED STATES PATENT AND TRADEMARK OFFICE
CERTIFICATE OF CORRECTION

PATENT NO.        : 8,735,321 B2                                      Page 1 of 1
APPLICATION NO.   : 12/990704
DATED             : May 27, 2014
INVENTOR(S)       : Ulrike Troppmann et al.

It is certified that error appears in the above-identified patent and that said Letters Patent is hereby corrected as shown below:

In the Claims

In Claim 5,
Col. 26, lines 59-60, delete
"N-(3', 4'-trifluorobiphenyl-2-yl)-3-difluoromethyl- 1-methyl-1H-pyrazole-4-carboxamide"
and insert therefor
--N-(3', 4', 5',-trifluorobiphenyl-2-yl)-3-difluoromethyl- 1-methyl-1H-pyrazole-4-carboxamide--.

In Claim 14,
Col. 28, lines 5-7, delete
"N-(3',4',4',5'-trifluorobiphenyl-2-yl)-3-difluoromethyl-1-methyl-1H-pyrazole-- 4-carboxamide"
and insert therefor
--N-(3',4',5'-trifluorobiphenyl-2-yl)-3-difluoromethyl-1-methyl-1H-pyrazole- 4-carboxamide--.

In Claim 17,
Col. 28, lines 29-31, delete
"N-(3',4',5'-trifluorobiphenyl-2yl)-3-difluoromethyl-1-methyl-1H-pyrazole-4-carboxamide"
and insert therefor
--N-(3',4',5'-trifluorobiphenyl-2-yl)-3-difluoromethyl-1-methyl-1H-pyrazole-4-carboxamide--.

Signed and Sealed this
Thirtieth Day of June, 2015

Michelle K. Lee
*Director of the United States Patent and Trademark Office*